United States Patent [19]
Holman

[11] Patent Number: 4,950,699
[45] Date of Patent: Aug. 21, 1990

[54] WOUND DRESSING INCORPORATING COLLAGEN IN ADHESIVE LAYER

[75] Inventor: Daniel G. Holman, Sun Lakes, Ariz.

[73] Assignee: Genetic Laboratories, Inc., St. Paul, Minn.

[21] Appl. No.: 350,640

[22] Filed: May 11, 1989

Related U.S. Application Data

[63] Continuation of Ser. No. 142,713, Jan. 11, 1988, abandoned.

[51] Int. Cl.$^5$ .................. A61L 15/32; A61K 31/78; C08L 33/12; C08L 99/00
[52] U.S. Cl. .................... 524/21; 128/156; 424/81; 424/116; 424/443; 424/445; 514/953; 530/354; 530/356

[58] Field of Search .................. 128/156, 325; 424/81, 424/116, 283, 443, 445; 514/953; 522/64; 524/21; 530/354, 356

[56] References Cited

U.S. PATENT DOCUMENTS 4,746,514  5/1988  Warne .................................. 522/64

Primary Examiner—Thurman K. Page
Assistant Examiner—C. Azpuru
Attorney, Agent, or Firm—Haugen and Nikolai

[57] ABSTRACT

A composition and formulation for use in covering and healing of wounds to the body, the formulation consisting of a mixture of a tissue compatible, water-based acrylic adhesive and collagen. The formulation comprises from between about 0.1% and 10% of collagen (dry basis), with the adhesive component preferably containing about 50% solids, balance water.

11 Claims, No Drawings

WOUND DRESSING INCORPORATING COLLAGEN IN ADHESIVE LAYER

This is a continuation of application Ser. No. 07/142,713, filed Jan. 11, 1988, now abandoned.

BACKGROUND OF THE INVENTION

The present invention relates generally to an improved composition and formulation for use in covering and healing of wounds to the body, and particularly to a formulation consisting of a mixture of a tissue compatible, water based acrylic adhesive and collagen.

In the past, collagen hemostats have been used, particularly for the purpose of absorbing blood from wounds, either wounds caused by injury through trauma, or for bleeding as a result of surgical incisions. The collagen employed is prepared as a dry fibrous water-insoluble salt of purified bovine corium collagen. This material is normally dry and sterile, and is available as the partial hydrochloric acid salt. Such collagens are, of course, well known and widely commercially available.

Typically, this water-insoluble hydrochloric acid salt is prepared in a fibrous form, normally a loose fibrous form in a compacted web. The fibrils are subjected to thermal sterilization in a dry atmosphere.

When the collagen substance comes into contact with a bleeding surface, platelets are attracted to the collagen and coagulation is accelerated. This acceleration is believed due to the aggregation of platelets into the collagen-rich zone. Such phenomena are, of course, well known, with the utilization of collagen for such treatment being recognized as a standard procedure.

SUMMARY OF THE INVENTION

In connection with the present invention, however, collagen is introduced into the area adjacent the wound site by being placed in admixture in a formulation containing a water-soluble acrylic based adhesive. A body-compatible water soluble acrylic based adhesive is employed to maintain continuous and constant contact between the wound site and collagen contained in the formulation. The availability of the collagen component at the wound site, particularly when maintained in admixture with a water based acrylic adhesive has been found to produce good results, and to aid in the covering and healing of wounds.

Therefore, it is a primary object of the present invention to provide an improved formulation for aiding in the covering and healing of wounds to the body, the formulation consisting essentially of a mixture of collagen and an adhesive compatible with tissue surfaces, the collagen component normally being in the form of water-insoluble partial hydrochloric acid salt of purified bovine collagen, and with the adhesive being in the form of an acrylic water-based adhesive compatible with tissue surfaces of the body.

It is therefore a primary object of the present invention to provide an improved collagen-adhesive formulation which may be applied directly to the wound, with the formulation aiding in the covering and healing of wounds inflicted either through trauma or through surgical procedures.

It is yet a further object of the present invention to provide an improved formulation for aiding in the covering and healing of wounds to the body which consists of a mixture of sterilized bovine collagen and an acrylic water-based adhesive compatible with the tissue surfaces of the body.

Other and further objects of the present invention will become apparent to those skilled in the art upon a study of the following specification and appended claims.

DESCRIPTION OF THE PREFERRED EMBODIMENTS

In order to better comprehend the various aspects of the present invention, the following specific examples are provided:

EXAMPLE I

A water based acrylic adhesive is placed in admixture with a collagen in powder form pursuant to the following formulation:

| COMPONENT | PERCENT BY WEIGHT |
|---|---|
| Collagen (water insoluble partial hydrochloric acid salt) | 5%, dry basis |
| Water base acrylic adhesive in 50:50 water mixture | 95%. |

The collagen, as indicated, is derived from bovine, particularly bovine hides and is, of course, commercially available. The water base acrylic adhesive is also commercially available, specifically from Semex Medical, a subsidiary of Seton Company of Malvern, Pa. under the product No. "MD-0129".

EXAMPLE II

| COMPONENT | PERCENT BY WEIGHT |
|---|---|
| Collagen (water insoluble partial hydrochloric acid salt) | 10%, dry basis |
| Water base acrylic adhesive in 50:50 water mixture | 90%. |

As indicated hereinabove, the formulations as set forth in Examples I and II provide a convenient and desirable system for covering and healing of wounds to the body.

In the formulations of Examples I and II, the following information is provided:

TABLE I

| Component | Percent By Weight In The Formulation |
|---|---|
| Collagen (water insoluble partial hydrochloric acid salt) | 0.1%–10% |
| Water base acrylic adhesive in 50:50 water mixture | balance of 90%–99.9%. |

In accordance with the present invention, and as set forth hereinabove, the formulations of the present invention find particular utility in being placed into contact with the site of the wound to aid in both covering and healing the wound. Accordingly, intimate contact is achieved between the materials and no other form of attachment or application is necessary. Use of adhesive-type plasters and the like are not required.

While the formulations as set forth hereinabove are typically applied directly to the wound site without requiring backing, in certain instances, it may be desired to utilize a water permeable backing sheet to promote integrity for the collagen-adhesive mix. For example, a water-soluble adhesive together with a water-permeable backing sheet may be employed. When hydrated, the water-permeable backing sheet normally becomes transparent to permit the site of the wound to be viewed. The advantages available are a see-through feature for the material, as well as adhesion and a reduction in the rate of fluid loss from the wound.

The transparent or semi-transparent film may be fabricated from polyurethane or water stabilized collagen or a combination of these or other backings, with such films being, of course, commercially available and appropriate approved for direct contact to the tissue.

It will be understood and appreciated that the examples given herein are for purposes of illustration only, and are not to be construed as limitations upon the reasonable scope of the invention.

I claim:

1. A wound dressing composition to be applied to a wound to reduce bleeding and aid healing consisting substantially of:
    an amount of bodily tissue compatible, water based acrylic adhesive material consisting of a blend of copolymers of N-butyl acrylate and acrylamide and a copolymer of N-butyl acrylate and methyl methacrylate adapted to removably adhere to the tissue surface of the body adjacent a wound;
    an amount of collagen in homogeneous admixture with said formulation in an amount ranging between about 0.1% and 10% by weight of collagen on a dry basis in said adhesive; and
    wherein said adhesive establishes and maintains contact between the collagen and the tissue at said wound site when the admixture is applied thereto.

2. The composition of claim 1 particularly characterized in that said collagen is added in the form of a water insoluble hydrochloric acid salt.

3. The composition of claim 1 particularly characterized in that said water based acrylic adhesive is incorporated in the composition in the form of a gel containing approximately 50% acrylic adhesive solids, and the balance is water.

4. The composition of claim 2 particularly characterized in that said water based acrylic adhesive is incorporated in the composition in the form of a gel containing approximately 50% acrylic adhesive solids, and the balance is water.

5. The composition of claim 2 particularly characterized in that said collagen is bovine collagen.

6. A covering for aiding healing of a wound of interest in a tissue surface of the body which consisting substantially of:
    a backing material, said backing material being at least large enough to cover the wound of interest and overlap a portion of the tissue surface adjacent thereto and in the form of a microscopically fibrous and porous film; and
    a wound dressing composition for adhering said backing to the tissue surface of the body and to be applied directly to the wound to reduce bleeding and aid healing, said dressing composition further comprising;
    an amount of body tissue compatible water based acrylic adhesive material consisting of a blend of copolymers of N-butyl acrylate and acrylamide and a copolymer of N-butyl acrylate and methyl methacrylate on said backing adapted to adhere to said backing material and removably adhere to the tissue surface of the body adjacent a wound; and
    an amount of collagen in homogeneous admixture with said adhesive wherein said collagen is contained in said formulation in an amount ranging between 0.1% and 10% by weight of collagen on a dry basis in said adhesive; and
    wherein said adhesive establishes and maintains contact between said collagen and the tissue at said wound site upon application of said covering to said tissue surface.

7. The covering of claim 6 particularly characterized in that said collagen is added in the form of a water insoluble hydrochloric acid salt.

8. The covering of claim 5 particularly characterized in that said water based acrylic adhesive is incorporated in the composition in the form of a gel containing approximately 50% acrylic adhesive solids, the balance water.

9. The covering of claim 8 particularly characterized in that said collagen is added in the form of a water insoluble hydrochloric acid salt.

10. The covering as defined in claim 6 being particularly characterized in that said microscopically fibrous, porous film is semitransparent and consists essentially of a loosely woven sheet of water stabilized collagen.

11. The covering as defined in claim 6 being particularly characterized in that said microscopically fibrous, porous film is semitransparent and consists essentially of a combination of polyurethane fibrous collagen.

* * * * *